United States Patent [19]
Filbin

[11] Patent Number: 5,932,542
[45] Date of Patent: Aug. 3, 1999

[54] COMPOSITION AND METHODS USING MYELIN-ASSOCIATED GLYCOPROTEIN (MAG) AND INHIBITORS THEREOF

[75] Inventor: Marie T. Filbin, New York, N.Y.

[73] Assignee: Research Foundation of CUNY, Hunter College, New York, N.Y.

[21] Appl. No.: 08/670,511

[22] Filed: Jun. 27, 1996

Related U.S. Application Data

[60] Provisional application No. 60/000,561, Jun. 27, 1995.
[51] Int. Cl.⁶ .......................... A61K 38/02; A61K 39/395
[52] U.S. Cl. ............................................. 514/8; 424/133.1
[58] Field of Search ........................ 514/2, 8; 424/133.1

[56] References Cited

U.S. PATENT DOCUMENTS 5,250,414  10/1993  Schwab .................................. 435/7.72

FOREIGN PATENT DOCUMENTS

WO 95/22344  8/1995  WIPO .

OTHER PUBLICATIONS

Bartsch, L. et al., "Lack of evidence that the myelin–associated glycoprotein is a major inhibitor of axonal regeneration in the CNS," *Neuron*, 15, pp. 1375–1381 (1995).
Bregman, B.S., et al., "Recovery from spinal cord injury mediated by antibodies to neurite growth inhibitors," *Nature*, 378, pp. 498–501 (1995).
Caroni, P., et al., "Antibody against myelin–associated inhibitor of neurite growth neutralizes nonpermissive substrate properties of CNS white matter," *Neuron*, 1, pp. 85–96 (1988a).
Caroni, P., et al., "Two membrane protein fractions from rat central myelin with inhibitory properties for neurite growth and fibroblast spreading," *J. Cell Biol.*, 106, pp. 1281–1288 (1988b).
DeBellard, M.E., et al., "Myelin–associated glycoprotein inhibits axonal regeneration from a variety of neurons via interaction with a sialoglycoprotein," *Mol. Cell. Neurosci.*, 7, pp. 89–101 (1996a).
DeBellard, M.E., et al., "Inhibition of axonal regeneration by myelin involves a neuronal sialoglycoprotein," *Soc. Neurosci. Abs.*, 130.5 (1996b).
Doherty, P., et al., "A threshold effect of the major isoforms of NCAM on neurite outgrowth," *Nature*, 343, pp. 464–466 (1990).
Doherty, P., et al., "Neurite outgrowth in response to transfected NCAM changes during development and is modulated by polysialic acid," *Neuron*, 5, pp. 209–219 (1990).
Filbin, M.T., "Myelin–associated glycoprotein: a role in myelination and in the inhibition of axonal regeneration," *Curr. Opin. Neurobiol.*, 5, pp. 588–595 (1995).
Fruttiger, M., et al., "Crucial role for the myelin–associated glycoprotein in the maintenance of axonal–myelin integrity," *Eur. J. Neurosci.*, 7, pp. 511–515 (1995).
Johnson, P.W., et al., "Recombinant myelin associated glycoprotein confers neural adhesion and neurite outgrowth function," *Nueron*, 3, pp. 377–385 (1989).

Kelm, S., et al., "Sialoadhesin, myelin–associated glycoprotein and CD22 define a new family of sialic acid–dependent adhesion molecules of the immunoglobulin superfamily," *Curr. Bio.*, 4, pp. 965–972 (1994).
Luo, Y., et al., "Collapsin: a protein in brain that induces the collapse and paralysis of neuronal growth cones," *Cell*, 75, pp. 217–227 (1993).
McKerracher, L., et al., "Identification of myelin–associated glycoprotein as a major myelin–derived inhibitor of neurite outgrowth," *Neuron*, 13, pp. 805–811 (1994).
Mukhopadhyay, G., et al., "A novel role for myelin–associated glycoprotein as an inhibitor of axonal regeneration," *Neuron*, 13, pp. 757–767 (1994).
Ng, W.P., et al., "Myelin from MAG——deficient mice is a strong inhibitor of neurite outgrowth," *NeuroReport*, 7, pp. 861–864 (1996).
Poltorak, M., et al., "Myelin–associated glycoprotein, a member of the L2/HNK–1 family of neural cell adhesion molecules, is involved in neuron–oligodendrocyte and oliogodendrocyte interaction," *J. Cell Biol.*, 105, pp. 1897–1899 (1987).
Schafer, M., et al., "Disruption of the gene for the myelin–associated glycoprotein improves axonal regrowth in C57BL/Wld mice," *Neuron*, 16, pp. 1107–1113 (1996).
Schnell, L., et al., "Axonal regeneration in the rat spinal cord produced by an antibody against meylin–associated neurite growth inhibitors," *Nature*, 343, 269–272 (1990).
Schnell, L., et al., "Neurotrophin–3 enhances sprouting of corticospinal tract during development and after adult spinal cord lesion," *Nature*, 367, pp. 170–173 (1994).
Shen, Y., et al., "MAG expressed by Schwann cells inhibits axonal growth and branching," *Soc. Neurosci. Abs.* 130.6 (1996).

(List continued on next page.)

*Primary Examiner*—Alan L. Rotman
*Assistant Examiner*—Charanjit S. Aulakh
*Attorney, Agent, or Firm*—Fish & Neave; James F. Haley, Jr.; Barbara A. Ruskin

[57] ABSTRACT

This invention relates to the novel identification of myelin-associated glycoprotein ("MAG") as a potent inhibitor of neural regeneration. More particularly, this invention relates to compositions and methods useful for reversing inhibition of neural regeneration in the central and peripheral nervous system. Assays to monitor the effects of MAG on neural regeneration and to identify agents which will block or promote the inhibitory effects of MAG on neural outgrowth are provided. Screening methods for identifying such agents are also provided. This invention also relates to compositions and methods using agents that can reverse the inhibitory effects of MAG on neural regeneration. Methods for regulating and for promoting neural growth or regeneration in the nervous system, methods for treating injuries or damage to nervous tissue or neurons, and methods for treating neural degeneration associated with disorders or diseases, comprising the step of administering at least one of the compositions according to this invention are provided.

13 Claims, 12 Drawing Sheets

OTHER PUBLICATIONS

Tang, S., et al., "Only MAG of the sialoadhesins inhibits axonal regeneration," *Soc. Neurosci. Abs.* 130.8 (1996a).

Yang, L.J., et al., "Gangliosides are neuronal ligands for myelin–associated glycoprotein," *Proc. Nat. Acad. Sci. (USA)*, 93, pp. 814–818 (1996).

Doherty et al., "A Soluble Chimeric Form of the L1 Glycoprotein Stimulates Neurite Outgrowth," *Neuron*, 14(1), PP. 57–66 (Jan. 1995).

Filbin et al., "MAG as an Inhibitor of Neurite Outgrowth," 26th Meeting of the Am. Soc. for Neurochemistry, Santa Monica, CA, USA, Mar. 5–9, 1995. *J. Neurochem.*, 64 (Suppl. 2), S41 (1995).

Filbin et al., "The Effect of Myelin–Associated Glycoprotein on Neurite Outgrowth is Dependent on the Interaction with a Neuronal Sialo–Glycoprotein," International Symposia on Myelin and Myelin–Forming Cells, Okazaki, Japan, Jul. 8–10, 1995, *Dev. Neuroscience*, 17(3), p. 183, XP 000605479.

Matsuda et al., "Soluble myelin–associated glycoprotein––immunoglobulin G1 chimera protein promotes neurite outgrowth from mouse cerebellar neurons," *Neuroscience Letters*, 205, pp. 87–90 (1996).

COMPOSITION AND METHODS USING MYELIN-ASSOCIATED GLYCOPROTEIN (MAG) AND INHIBITORS THEREOF

Benefit of United States Provisional Application No. 60/000,561, filed Jun. 27, 1995, is claimed herefor.

TECHNICAL FIELD OF THE INVENTION

This invention relates to the novel identification of myelin-associated glycoprotein ("MAG") as a potent inhibitor of neural regeneration. More particularly, this invention relates to compositions and methods useful for reversing inhibition of neural regeneration in the central and peripheral nervous system. Assays to monitor the effects of MAG on neural regeneration and to identify agents which will block or promote the inhibitory effects of MAG on neural outgrowth are provided. Screening methods for identifying such agents are also provided. This invention also relates to compositions and methods using agents that can reverse the inhibitory effects of MAG on neural regeneration. Methods for regulating and for promoting neural growth or regeneration in the nervous system, methods for treating injuries or damage to nervous tissue or neurons, and methods for treating neural degeneration associated with disorders or diseases, comprising the step of administering at least one of the compositions according to this invention are provided.

BACKGROUND OF THE INVENTION

The mammalian nervous system does not regenerate after injury despite the fact that there are many molecules present which encourage/promote axonal (nerve) growth. It is believed that the lack of regeneration caused by the presence of molecules in the central nervous system (CNS) and the peripheral nervous system (PNS) which actively prevent/inhibit regeneration. Hence, the well documented inability of the adult mammalian CNS to regenerate after injury is believed to result from a predominance of inhibitory molecules.

It has been demonstrated that when neurons are grown on tissue sections of the CNS they fail to extend processes onto areas of white matter, myelin. It is believed that myelin-specific inhibitory molecules can largely account for the lack of CNS regeneration and their identification will help in the design of therapies to encourage regrowth after injury. The precise molecules responsible for this inhibition have, so far, remained elusive. If these inhibitory molecules can be identified and blocked, then neural regeneration can be encouraged.

Schwab and co-workers have identified two components in CNS myelin, in the molecular weight ranges of approximately 35 kD and 250 kD, which arrest axonal growth. The most compelling observation in support of the inhibitory action of these two protein fractions is that antibodies raised to proteins eluted from these regions of polyacrylamide gels after separation of CNS myelin proteins, specifically reverses the inhibitory effect of myelin in vitro and allows limited spinal cord regeneration when applied in vivo to transected nerves (Caroni, P. and Schwab, M. E., Neuron, 1, pp. 85–96 (1988a); J. Cell Biol., 106, pp. 1281–88 (1988b); Schnell, L. and Schwab, M. E., Nature, 343, pp. 269–72 (1990)). The nature of these two proteins and how they act have not yet been described, but, it is generally accepted that they are significant contributors to the inhibitory effect of this tissue. However, as acknowledged by the authors, other factors are likely to contribute to the inhibition by CNS myelin as even in the presence of antibodies directed against these two proteins, the majority of axons in vivo fail to regenerate (Schnell, L. and Schwab, M. E., Nature, 343, pp. 269–72 (1990); Schnell et al., Nature, 367, pp. 170–73 (1993)).

In addition to inhibitory molecules in myelin, another family of proteins has recently been identified whose members inhibit axonal regeneration. These molecules are called collapsins (Luo et al., Cell, 75, pp. 217–27 (1993)). However, collapsins are found ubiquitously throughout the nervous system and as they are found in regions of the nervous system in which axons will grow, i.e. gray matter, they are unlikely to contribute significantly to the lack of neural regeneration after injury. Instead, the collapsins most likely play a role in guiding growing axons during development.

Previously it was shown that MAG, like many members of the Ig-superfamily of molecules, could promote neurite outgrowth, in this case, from dorsal root ganglion (DRG) neurons from 2 day old rats (Johnson et al., Neuron, 3, pp. 377–85 (1989)). We observed a similar effect on DRG neurons from rats up to postnatal day 3, but after this age MAG had the opposite effect, i.e., it inhibited neurite outgrowth (Mukhopadhyay et al., Neuron, 13, pp. 757–67 (1994)). Furthermore, we also found that MAG dramatically inhibited neurite outgrowth from cerebellar neurons from rats of all ages up to adult. Polyclonal antibodies directed against MAG could specifically block both stimulatory and inhibitory effects of MAG on neurite outgrowth. MAG, therefore, depending on the age and the type of neuron, can either promote or inhibit neurite outgrowth. Subsequent to our report on the inhibitory effects of MAG, another group demonstrated, using a different complementary approach, that MAG is an inhibitor of axonal growth (McKerracher et al., Neuron, 13, pp. 805–811 (1994); WO 95/22344 (Aug. 24, 1995); incorporated herein by reference).

It would be useful to block the inhibitors of axonal regeneration for treating patients with nervous system injuries where neural regeneration is a problem. No molecule had been identified in myelin which is a potent inhibitor of axonal regeneration. Although Schwab and co-workers identified components in myelin that are inhibitory, the precise nature of these components has not been identified, i.e., they have not been cloned nor have the proteins been purified. In addition, there was no information available on the component on the neuron that the putative inhibitory molecules interact with to prevent regrowth. As no inhibitory nor interacting molecules had been precisely identified, it was difficult, if not impossible, to logically design strategies whereby these molecules can been blocked and prevented from inhibiting neural regeneration.

SUMMARY OF THE INVENTION

The present invention solves the problems referred to above by identifying MAG as a potent inhibitor of axonal regeneration in the central nervous system (CNS) and the peripheral nervous system (PNS). The present invention provides compositions and methods for blocking or manipulating the levels of MAG activity in the nervous system.

In one embodiment, the compositions comprise a pharmaceutically acceptable carrier and a therapeutically effective amount of at least one inhibitor of MAG. Inhibitors of MAG include but are not limited to anti-MAG antibodies, altered and/or mutated forms of MAG characterized by an altered biological activity, free sialic acid-bearing sugars, modified derivatives of sialic acid attached to a sugar, a sialic acid-bearing sugar attached to a protein or lipid carrier molecule, a modified sialic acid-bearing sugar attached to a protein or lipid carrier molecule and a sialic acid glycopeptide.

In one preferred embodiment, the MAG inhibitor comprises a small sialic acid-bearing oligosaccharide (sugar), which is optionally a competitive inhibitor of sialidase. More preferably, the sialic acid analog is sialo 2,3-α lactose (2,3-SL) or 2,3-dideoxy sialic acid (DD-NANA).

In another preferred embodiment, the MAG inhibitor comprises an altered and/or mutant form of MAG which can inhibit the binding of endogenous MAG to neurons in the CNS or PNS. Altered forms of MAG preferably comprise all or a portion of the extracellular domain of MAG fused to another molecule which renders the chimeric protein soluble. One such preferred soluble MAG chimeric protein comprises the five Ig-like domains of MAG fused to the Fc domain of a human immunoglobulin molecule, such as IgG ("MAG-Fc").

Preferred altered/mutated forms of MAG are soluble molecules which harbor one or more mutations in the MAG molecule that reduce or eliminate its ability to inhibit or promote neurite outgrowth compared to endogenous MAG or MAG-Fc, but do not significantly diminish the binding of the altered or mutant form of MAG to neuronal surfaces. Most preferred altered/mutant forms of MAG are soluble molecules comprising a truncated form of MAG-Fc consisting of the first three of the five extracellular Ig-like domains of MAG fused to an immunoglobulin Fc domain ("MAG (d1–3)-Fc").

In another embodiment, the compositions comprise a therapeutically effective amount of an enzyme that can alter or remove sialic acid residues having a Neu5Acα2→3Galβ1→3GalNAc (3-O) structure, which mediate MAG binding to neuronal surfaces in the PNS or CNS. Preferred compositions of this embodiment comprise sialidase (a neuraminidase) and sialyl transferases that alter the structure and/or lower the effective concentration of Neu5Acα2→3Galβ1→3GalNAc ("3-O") sialyated glycans.

The present invention also provides methods for regulating and for promoting neural growth or regeneration in the nervous system, methods for treating injuries or damage to nervous tissue or neurons, and methods for treating neural degeneration associated with disorders or diseases, comprising the step of administering at least one of the pharmaceutical compositions according to this invention.

The present invention provides an assay for determining whether neurite outgrowth from a particular type of neuron at a particular age is stimulated or inhibited in the presence of MAG (or a MAG derivative). In one embodiment, the method comprises the steps of:
 a) culturing a first sample of a selected neuronal cell type on a growth-permissive substrate in the absence of MAG;
 b) culturing a second sample of the selected neuronal cell type on a growth-permissive substrate comprising bound MAG; and
 c) comparing the relative amount of neurite growth in the cultured cells of a) and b); wherein when the relative growth of neurites in the cultured cells of a) is greater than in b), the neuronal cell is inhibited by the presence of MAG, and when the relative growth of neurites in the cultured cells of a) is less than in b), the neuronal cell is stimulated by the presence of MAG.

In a preferred embodiment, the growth-permissive substrate in the absence of MAG comprises a monolayer of mammalian cells that do not express cell-surface MAG, and the growth-permissive substrate comprising bound MAG comprises a monolayer equivalent mammalian cells engineered to express cell surface MAG. Preferably, the mammalian cells are CHO cells engineered to express cell surface MAG, such as CHO-MAG2 cells.

The present invention also provides methods for identifying a MAG-dependent neurite growth altering agent, i.e., an agent which alters neurite outgrowth from a selected neuronal cell type, or population of mixed cell types, in the presence of MAG compared to the absence of MAG.

In one embodiment, the method comprises the steps of:
 a) culturing a first sample of a selected neuronal cell type on a growth-permissive substrate in the absence of MAG;
 b) culturing a second sample of the selected neuronal cell type on a growth-permissive substrate comprising bound MAG in an amount sufficient to alter neurite outgrowth from the cells compared to the first sample of cells cultured in the absence of MAG;
 c) incubating the cell cultures of a) and b) with a known relative concentration of a test agent for a time sufficient to allow neurite growth; and
 d) comparing the relative amount of neurite growth in the cultured cells of a) and b); wherein an agent that changes the relative growth of neurites in the cultured cells of a) and b) is identified as a MAG-dependent neurite growth altering agent.

In a preferred embodiment, the growth-permissive substrate in the absence of MAG comprises a monolayer of mammalian cells that do not express cell-surface MAG, and the growth-permissive substrate comprising bound MAG comprises a monolayer equivalent mammalian cells engineered to express cell surface MAG. Preferably, the mammalian cells are CHO cells engineered to express cell surface MAG, such as CHO-MAG2 cells.

In another embodiment of this invention, the method for identifying a MAG-dependent neurite growth altering agent comprises the steps of:
 a) culturing separate samples of a selected neuronal cell type on a growth-permissive substrate lacking MAG;
 b) culturing a first sample of a) with a known concentration of a traceable, soluble form of MAG;
 c) culturing a second sample of a) with a known concentration of a traceable, soluble form of a control protein lacking MAG activity;
 d) incubating the cultures of b) and c) with a known relative concentration of a test agent for a time sufficient to allow neurite growth; and e) comparing the relative amount of neurite growth in the cultured cells of c) and d); wherein an agent that changes the relative growth of neurites in the cultured cells of c) and d) is identified as a MAG-dependent neurite growth altering agent.

In one preferred embodiment, the growth-permissive substrate lacking MAG comprises a monolayer of mammalian cells that do not express cell-surface MAG, such as COS or NIH 3T3 cells. In another preferred embodiment, the growth-permissive substrate lacking MAG comprises an immobilized monolayer of a purified, growth-promoting factor. One most preferred neuronal growth-promoting factor which may be immobilized onto a monolayer is the L1 glycoprotein.

In preferred embodiments, the soluble form of MAG is a MAG-Fc fusion protein, and the soluble control protein lacking MAG activity is a MUC 18-Fc fusion protein. Preferred traceable fusion proteins are radioactively or fluorescently labeled.

DETAILED DESCRIPTION OF THE INVENTION

Figure 1:
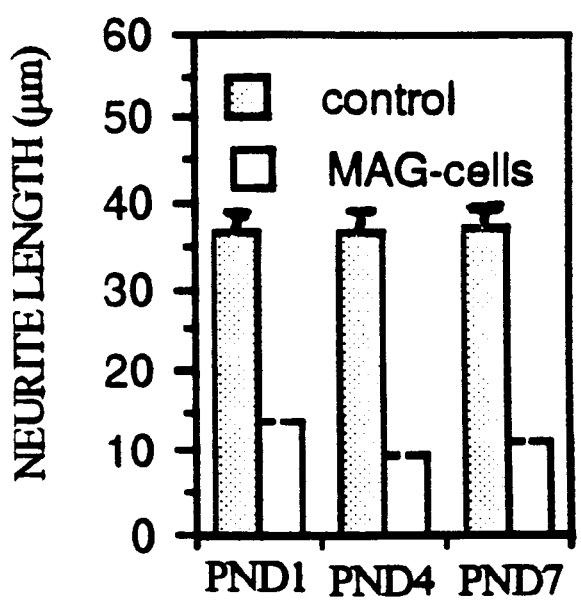
FIG. 1. Inhibition of Neurite outgrowth from Cerebellar Neurons by MAG. Cerebellar neurons from post-natal day (PND) 1, 4 and 7 were grown overnight on a monolayer of MAG-expressing (clear bars) or control transfected CHO cells (hatched bars). Neurons were stained for GAP-43 antigen and neurite length was measured and the average length calculated from at least 150 measurements (±SEM).

In order that the invention herein described may be fully understood, the following detailed description is set forth.

The term "MAG derivative" refers to a molecule comprising at least one MAG extracellular domain, wherein the MAG molecule has been altered (e.g., by recombinant DNA techniques to make chimera with portions of other molecules fused to the MAG molecule, or by chemical or enzymatic modification) or mutated (e.g., internal deletions, insertions, rearrangements and point mutations). MAG derivatives, unless otherwise noted, retain MAG activity.

The terms "MAG bioactivity" and "MAG biological activity" refer to the ability of a molecule, especially an altered or mutant form of MAG, to inhibit or promote neurite outgrowth of a selected neuronal cell type of a particular age, as detected in a neurite outgrowth assay such as those described herein, in qualitatively the same direction as cell-surface or soluble MAG.

The term "MAG binding activity" refers to the ability of a molecule, especially an altered or mutant form of MAG, to compete with cell-surface MAG or soluble MAG for sialic-acid dependent neuron binding in an assay such as those described herein. For example, preferred inhibitors of MAG retain MAG binding activity but have reduced or absent MAG bioactivity.

The term "MAG activity" refers generically to MAG bioactivity and binding activity as described above.

The term "modified derivative of sialic acid" refers to a sialic acid residue that has been modified chemically or enzymatically, especially to add or exchange chemical groups or side chains onto reactive positions of the molecule. Sialic acids are a family of nine-carbon acidic sugars which are derivatives of neuraminic acid and which are often at the termini of cell-surface carbohydrates. "NeuAc" stands for N-acetylneuraminic acid; "GalNAc" stands for N-acetylgalactosamine.

MAG Is a Potent Inhibitor of Neurite Outgrowth

As described above, MAG had been shown previously to promote neurite extension from particular types of neurons. In addition, MAG was believed to be involved in the initiation of myelin formation. The present invention demonstrates a novel role for MAG as an inhibitor of axonal outgrowth and hence of nerve regeneration in the central nervous system (CNS) and the peripheral nervous system (PNS).

Selected neuronal cell types may be isolated from animals at increasing times in postnatal days (PND) according to the procedures described in Example 1. Neurons representing a single cell type may be isolated and tested alone, or if desired, mixed populations of cells comprising one or more neuronal cell types in the presence or absence of non-neuronal cells may also be tested.

The present invention provides an in vitro assay for determining whether neurite outgrowth from a particular type of neuron at a particular age is stimulated or inhibited in the presence of MAG. Isolated neurons of choice may be cultured on a monolayer comprising a growth-permissive substrate in the presence or absence of bound MAG, and comparative neurite outgrowth may be measured. Preferably the growth-permissive substrate comprises mammalian fibroblast cells which have been engineered to express MAG on their cell surfaces. MAG-expressing cells may be engineered using the procedures described in Example 2. Neurite outgrowth on MAG-expressing cells may then be compared to neurite outgrowth on control cells that do not express cell-surface MAG.

As shown in FIG. 1, MAG is a potent inhibitor of axonal growth from cerebellar neurons from all ages of rats tested, newborn to adult. This was determined by co-culturing the neurons on transfected Chinese hamster ovary (CHO) cells expressing MAG and comparing the length of the neurites extended to those extended on control transfected CHO cells not expressing MAG (see Example 2). Four different MAG-expressing cell lines were used and each had the same effect and inhibited neurite outgrowth by at least 70% compared to control cells at all ages tested (FIG. 1; see also Mukhopadhyay et al., *Neuron*, 13, pp. 757–67 (1994)). The reversal of neurite growth inhibition by anti-MAG antibodies and the lack of effect of CHO cells expressing another myelin protein, Po, on neurite outgrowth demonstrates that this inhibition is specific to MAG (Mukhopadhyay et al., supra). However, as discussed above, it had been reported previously that MAG promotes neurite outgrowth from newborn DRG neurons (Johnson et al., *Neuron*, 3, pp. 377–385 (1989)).

Figure 2:
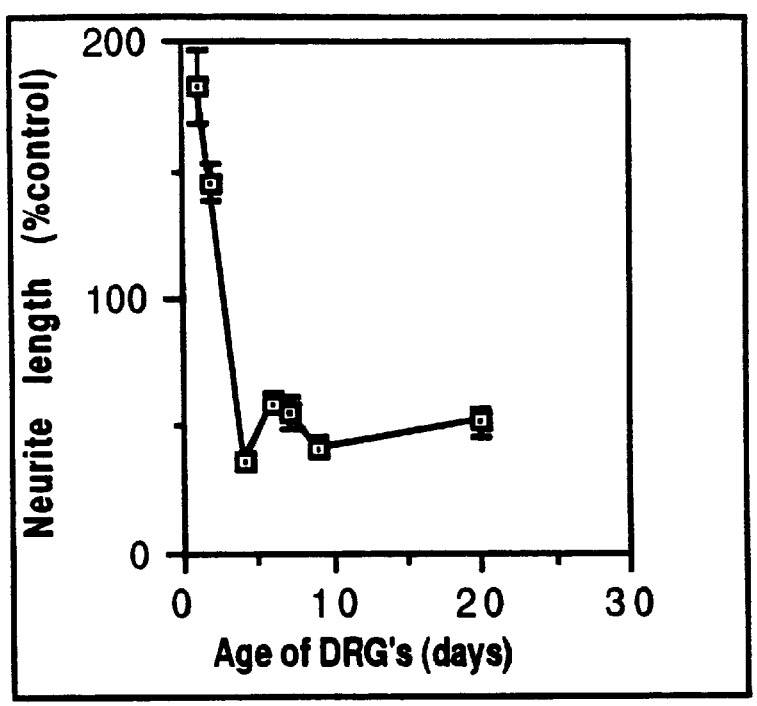
FIG. 2. Effect of NAG on Neurite Outgrowth from DRG Neurons of Different Ages. DRG neurons were isolated from animals from PND 1 to PND 20 and grown on MAG-expressing or control CHO cells and neurite length was calculated as described in FIG. 1.

To clarify this apparent discrepancy, dorsal root ganglia (DRG) neurons from one- to twenty-day old rats were tested in the neurite outgrowth assay on CHO cells as described in Example 2. As shown in FIG. 2, MAG enhanced neurite outgrowth of DRG neurons from two-day old rats; neurites were almost twice as long on MAG-expressing cells compared to control cells. On the other hand, when DRG neurons from adult rats were tested, MAG inhibited neurite outgrowth by about 40%. A more detailed time course of the effect of MAG on neurite outgrowth from DRG neurons of different ages revealed that the transition from promotion to inhibition takes place at about post-natal day 4 (FIG. 2). Hence, depending on the age and the type of neuron, MAG can either promote or inhibit neurite outgrowth.

MAG inhibits axonal outgrowth from many types of neurons

Figure 3:
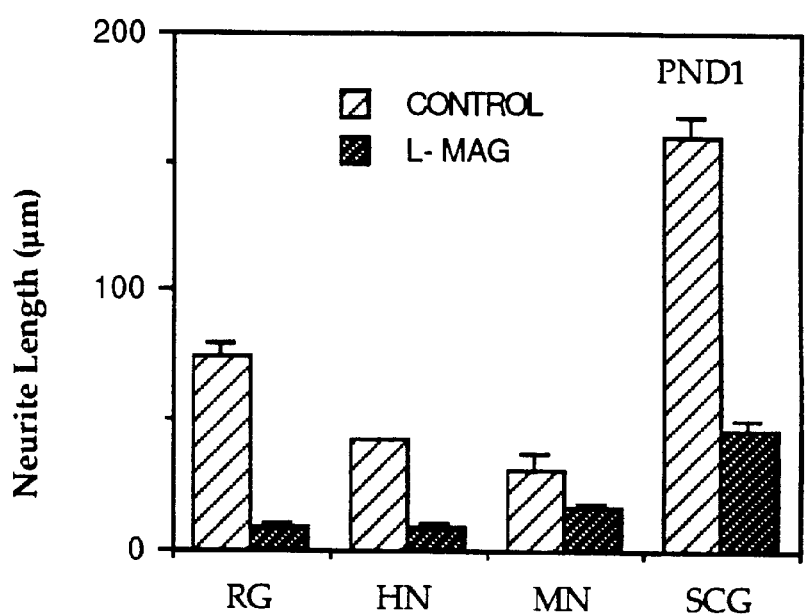
FIG. 3. Effect of MAG on Neurite Outgrowth from Different Neuronal Cell Types. Various neurons from PND1 animals were isolated and grown overnight on MAG-expressing (dark hatched) or control (light hatched) CHO cells. Average neurite length was calculated as described in FIG. 1. RG=retinal ganglion; HN=hippocampal; MN=motor; and SCG=superior cervical ganglion neurons.

Characterization of the effect of MAG on a variety of neuronal populations would aid in defining the requirements for enhanced regeneration after injury in various regions of the nervous system. To establish how other populations of neurons behave in response to MAG, various different neuronal cell types were isolated from one-day old rats (PND1) as described in Example 1. Isolated retinal ganglion (RG), hippocampal (HN), motor neurons (MN) and superior-cervical ganglion (SCG) were tested in CHO cell neurite outgrowth assays as described in Example 2. As shown in FIG. 3, MAG is a potent inhibitor of neurite growth in all cell types tested. Thus, MAG likely plays an important role in the lack of neural regeneration in all areas of the nervous system tested to date.

These results show that the transfected mammalian cell assay described in Example 2 is an effective assay whereby both the inhibition and promotion of neurite outgrowth by MAG can be monitored and characterized. This assay can also be used to screen and identify agents that can block (or enhance) MAG bioactivity, thereby altering its inhibition or stimulation of axonal outgrowth in the nervous system (Example 3). Such agents are called herein "MAG-dependent neurite growth altering agents."

Figure 4:
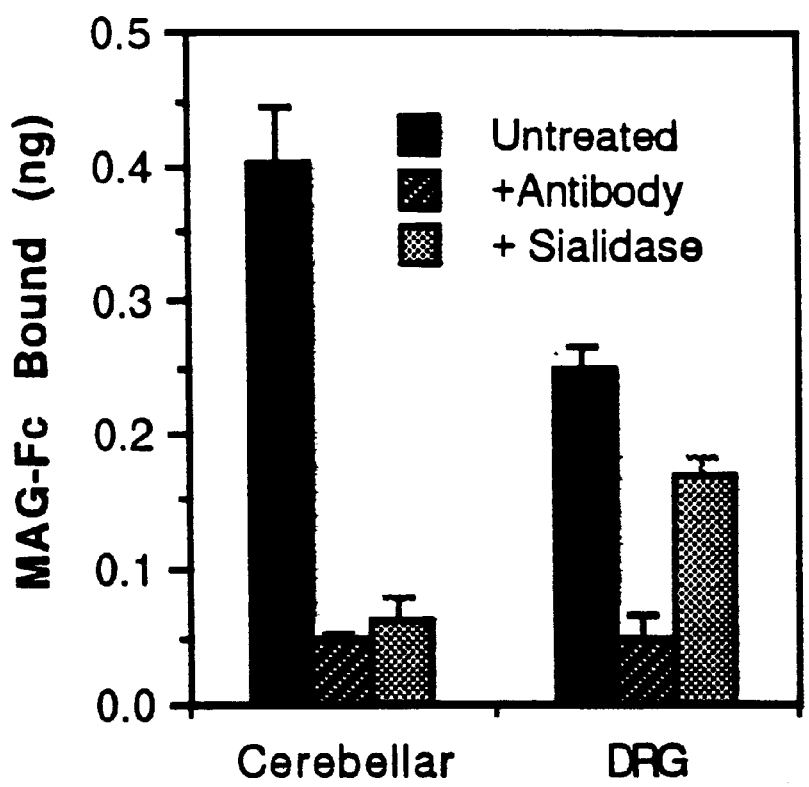
FIG. 4. Sialic acid-dependent Binding of MAG to Cerebellar and DRG Neurons. Radiolabelled MAG-Fc (solid bars) was allowed to bind to PND 1 cerebellar and DRG neurons. Incubations were also carried out in the presence of 5 µg/ml of MAG 513 monoclonal antibody (dark hatched bars) or with neurons that had been desialyated (speckled bars). Each experiment was carried out in quadruplicate. The results are the mean of 3 experiments.

MAG inhibits axonal outgrowth by binding to a sialic acid-bearing glycoprotein on neurons MAG binds to all types of neurons tested in a sialic acid-dependent fashion (Kelm et al., *Curr. Biol.*, 4, pp. 965–72 (1994)). FIG. 4 shows the results of an aqueous MAG-Fc neuron binding assay which was performed essentially as described in Kelm et al. This experiment confirms that the binding of MAG to isolated PDN1 cerebellar neurons (whose outgrowth is inhibited by MAG) is abolished either by inclusion of anti-MAG monoclonal antibody 513 or by sialidase treatment of neurons before the binding reactions. Sialidase is an enzyme which removes sialic acid from glycoconjugates. Similarly, the binding of MAG to isolated PDN1 DRG neurons (whose outgrowth is promoted by MAG) is inhibited by inclusion of anti-MAG monoclonal antibody 513 and to as lesser extent, by sialidase treatment.

Figure 5:
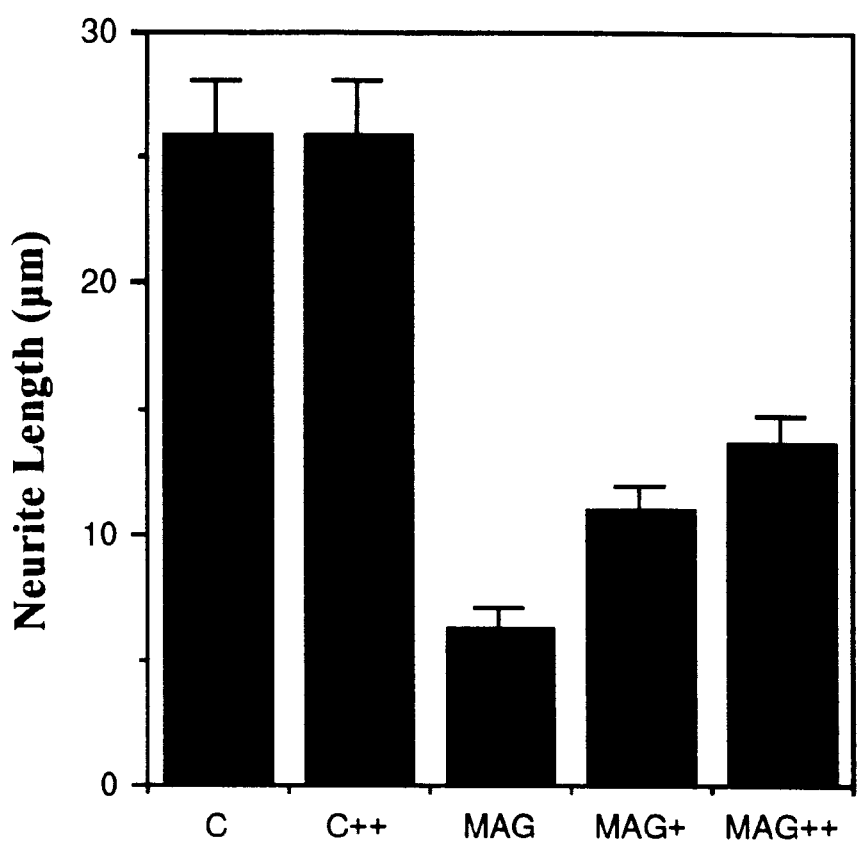
FIG. 5. Desialation of Neurons Blocks the Inhibition of Neurite Outgrowth by MAG. Neurite outgrowth was compared, as described in FIG. 1, for cerebellar neurons from PND 2 animals on MAG-expressing and control CHO cells, with and without desialation of the neurons before the assay. C=neurons grown on control CHO cells; MAG= neurons grown on MAG-expressing CHO cells; +=neurons were desialyated prior to the assay; ++=neurons were desialyated prior to the assay and desialidase was included in the cultures. Results represent the average neurite length (µm) from at least 150 neurons±SEM.
Figure 6:
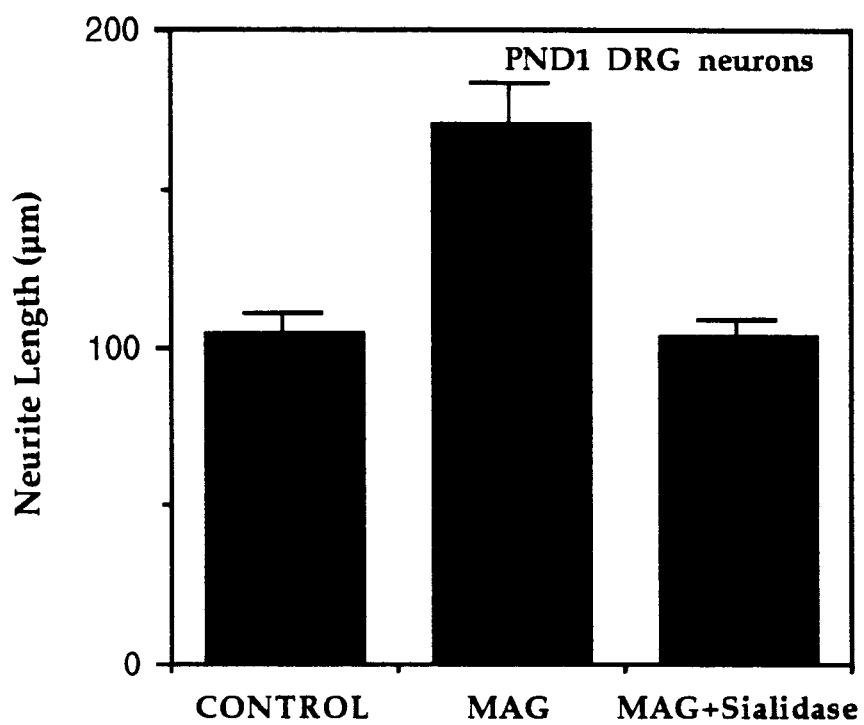
FIG. 6. Desialation of Neurons Blocks the Promotion of Neurite outgrowth by MAG. Neurite outgrowth was compared, as described in FIG. 1, for DRG neurons from PND 1 animals on MAG-expressing (MAG) and control CHO cells (Control), with (MAG sialidase) and without desialyation of the neurons before the assay. Results represent the average neurite length (µm) from at least 150 neurons±SEM.

To determine if the sialic acid-dependent binding of MAG to neurons is the event that signals inhibition or promotion of axonal growth and regeneration, neurite outgrowth assays such as those described in Example 2 were performed after the isolated neurons had been treated with sialidase (Example 7). The inhibition of axonal regeneration was reversed by about 50% when PND2 cerebellar neurons were desialyated (FIG. 5). Similarly, when newborn (PND1) DRG neurons were desialyated, promotion of axonal outgrowth by MAG was completely abolished (FIG. 6).

Axonal outgrowth assays such as those described in Example 2 were also performed in the presence of small, free sialic acid-bearing sugars. These sugars can compete with the sialic acid components of the neuronal surface for MAG binding and thereby block the inhibition (TABLE 1) or promotion (TABLE 2) of neurite growth by MAG. Inclusion of increasing concentrations of either of the small sialic acid-bearing sugars 2,3-dideoxy sialic acid (DD-NANA) or sialo 2,3-α lactose (SL) reversed the inhibition of axonal growth by MAG by between 40–56% (TABLE 1) and abolished the promotion of neurite outgrowth by MAG completely (TABLE 2).

TABLE 1

SMALL SIALIC ACID-SUGARS BLOCK
THE INHIBITION OF AXONAL GROWTH BY MAG

| Sugar | Conc. (mM) | Cell | % Reversal of Inhibition |
|---|---|---|---|
| DD NANA | 0 | control | 0 |
| DD NANA | 20 | control | 0 |
| DD NANA | 0 | MAG | 0 |
| DD NANA | 1 | MAG | 15% |
| DD NANA | 10 | MAG | 45% |
| DD NANA | 20 | MAG | 64% |
| SL | 0 | control | 0 |
| SL | 9 | control | 0 |
| SL | 0 | MAG | 0 |
| SL | 1 | MAG | 11% |
| SL | 5 | MAG | 42% |
| SL | 9 | MAG | 26% |

Neurite outgrowth was compared for cerebellar neurons from PND 2 animals, grown on MAG-expressing and control CHO cells as describe in Example 3.

TABLE 2

SMALL SIALIC-ACID SUGARS BLOCK THE
PROMOTION OF AXONAL GROWTH BY MAG

| Sugar | Conc. (mM) | Cell | % Reversal of Promotion |
|---|---|---|---|
| DD NANA | 0 | control | 0 |
| DD NANA | 20 | control | 0 |
| DD NANA | 0 | MAG | 0 |
| DD NANA | 1 | MAG | 0 |
| DD NANA | 10 | MAG | 51% |
| DD NANA | 20 | MAG | 97% |
| SL | 0 | control | 0 |
| SL | 18 | control | 0 |
| SL | 0 | MAG | 0 |
| SL | 1 | MAG | 0 |
| SL | 5 | MAG | 96% |
| SL | 18 | MAG | 98% |

Neurite outgrowth was compared for DRG neurons from PND 2 animals, grown on MAG-expressing and control CHO cells as describe in Example 3.

The experiments described above demonstrate that MAG biological activity is normally dependent on the ability of MAG to bind to a sialic acid-bearing component on the surface of neurons. It is thus envisioned that a variety of agents that can disrupt the ability of MAG to bind to this sialic acid-bearing component will function in vivo as MAG inhibitors and will thus be useful for regulating, and especially for promoting neuronal growth in the CNS and PNS.

Inhibitors of MAG binding activity include but are not limited to anti-MAG antibodies, free sialic acid-bearing sugars, modified derivatives of sialic acid attached to a sugar, a sialic acid-bearing sugar attached to a protein or lipid carrier molecule, a modified sialic acid-bearing sugar attached to a protein or lipid carrier molecule and sialic acid glycopeptides or glycoproteins.

As shown above, inhibitors of MAG binding activity also include enzymes that can alter or remove sialic acid residues, especially those having a Neu5Acα2→3Galβ1→3GalNAc (3-O) structure, which mediates MAG binding to neuronal surfaces in the PNS or CNS. Preferred compositions of this embodiment comprise sialidase (a neuraminidase) and sialyl transferases that alter the structure and/or lower the effective concentration of Neu5Acα2→3Galβ1→3GalNAc ("3-O") sialyated glycans.

Identifying MAG-dependent Growth Regulating Agents

Putative new MAG-dependent neurite growth regulating agents may be tested using the procedures described in Example 3. A test agent is identified as a MAG inhibitor when it promotes neurite growth from a cell type inhibited by MAG or inhibits neurite growth from a cell type stimulated by MAG. Similarly, an agent is a MAG agonist when it promotes neurite growth from a cell type stimulated by MAG or inhibits neurite growth from a cell type inhibited by MAG.

Soluble MAG is a potent inhibitor of axonal regeneration

This invention provides a second method for assaying the effects of MAG on axonal growth and for identifying MAG-dependent neurite growth altering agents. The method involves culturing separate samples of a selected neuronal cell type on a growth-permissive substrate lacking MAG in the presence of either a known concentration of a traceable, soluble form of MAG or of a control protein lacking MAG activity. The neuron cultures are then incubated with a known relative concentration of a test agent for a time sufficient to allow neurite growth, and the amount of neurite growth in the cells cultured in the presence or absence of soluble MAG compared (Example 5). An agent that changes the relative growth of neurites from cells cultured in the presence and absence of soluble MAG is identified as a MAG-dependent neurite growth altering agent.

In a preferred embodiment, the growth-permissive substrate lacking MAG comprises a monolayer of mammalian cells that do not express cell-surface MAG, such as COS or NIH 3T3 cells. A wide variety of mammalian cell lines, such as fibroblast and epithelial cells, may be used and are well known to those of ordinary skill in the art. The present invention is not limited by the cell types which may be employed to make such growth-permissive monolayers that do not comprise bound MAG.

In another preferred embodiment, the growth-permissive substrate lacking MAG comprises an immobilized monolayer of a purified, growth-promoting factor. It is well known in the art that neuronal cells may be cultured on growth-promoting monolayers comprising collagen or fibronectin. A preferred neuronal growth-promoting factor according to the present invention which may be immobilized onto a monolayer is the L1 glycoprotein.

In preferred embodiments of this method, the soluble form of MAG is a MAG-FC fusion protein, and the soluble control protein lacking MAG activity is a MUC18-Fc fusion protein (Example 4). Preferred traceable fusion proteins are radioactively or fluorescently labeled using commercially available reagents and methods well known in the art.

Figure 7A:
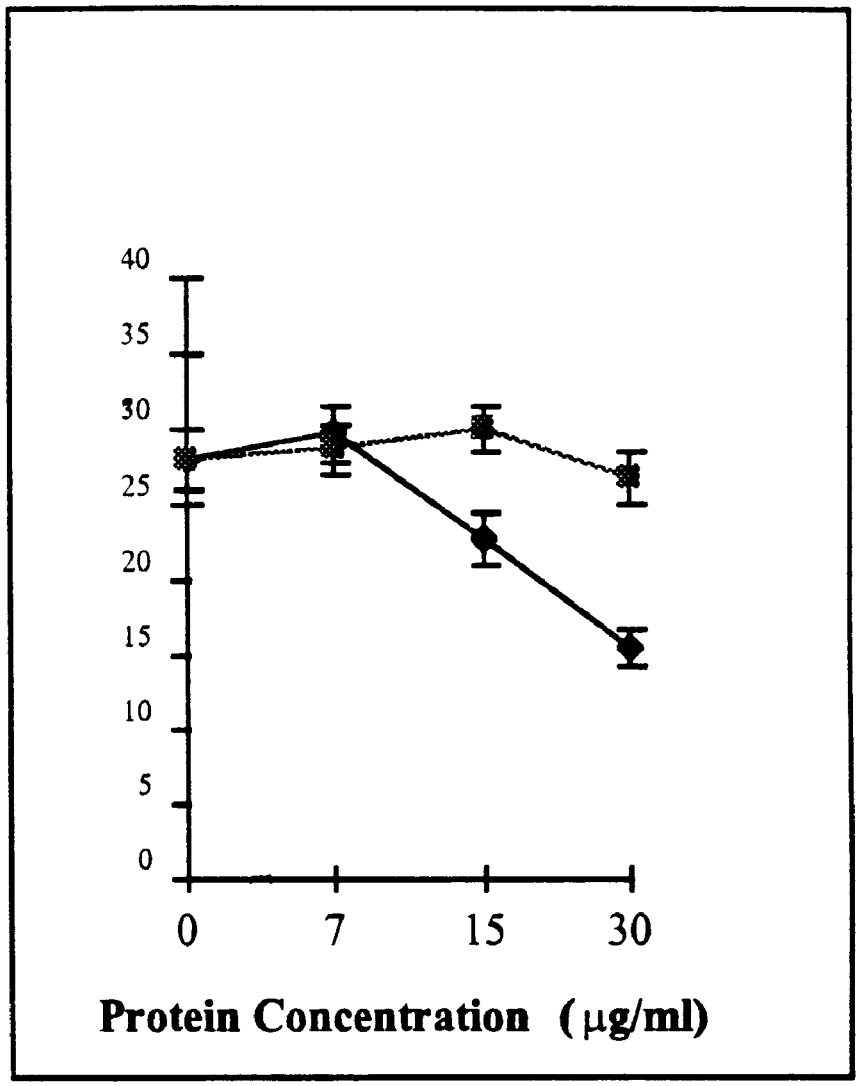
FIG. 7(a). Soluble MAG-Fc Inhibits Axonal Regeneration of Cerebellar Neurons Grown on L1 in a Concentration-dependent Manner. L1-Fc was immobilized and isolated PND2 cerebellar neurons were grown overnight in the presence of various concentrations of MAG-Fc (diamonds) or MUC-Fc (squares) as indicated. Neurons were fixed, stained and neurite length measured as described in FIG. 1. Results represent the average neurite length (µm)±SEM.
Figure 7B:
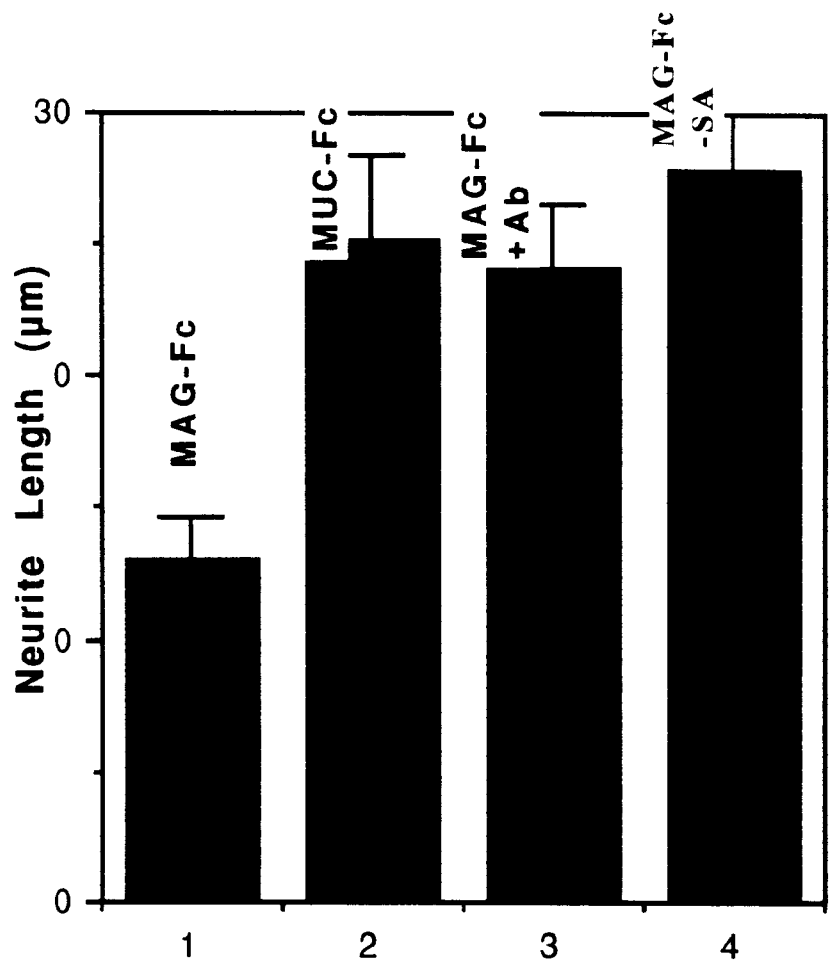
FIG. 7(b). MAG-Fc Inhibits Axonal Growth in a Specific, Sialic Acid-dependent Manner. Cerebellar neurons were grown on immobilized L1 as a substrate. MAG-Fc (column 1) or MUC-Fc (column 2) were added at a concentration of 50 µg/ml. Anti-MAG 513 monoclonal antibodies were included at a concentration of 5 µg/ml (column 3) or desialyated neurons were used (column 4). Neurite length (µm) was measured as described in FIG. 1. Results represent the average neurite length (µm)±SEM.
Figure 7C:
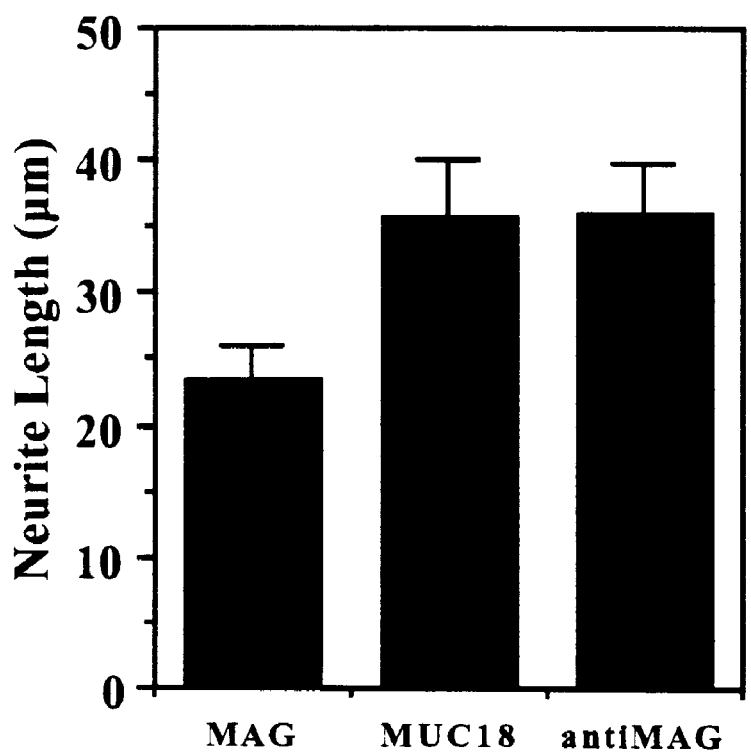
FIG. 7(c). MAG-Fc Inhibits Axonal Growth from Neurons Grown on Fibroblasts. Isolated PND 2 cerebellar neurons were grown on a substrate of fibroblasts (3T3 cells) in the presence of 50 µg/ml MAG-Fc (Column 1, MAG), 50 µg/ml of MUC18-Fc (column 2, MUC 18) or in the presence of 5 µg/ml anti-MAG 513 monoclonal antibodies (column 3, anti-MAG). Neurite length (µm) was measured as described in FIG. 1. Results represent the average neurite length (µm)±SEM.

FIG. 7a shows the results of an assay performed according to the procedures described in Example 4. In this assay, neurons were grown on a substrate comprising the purified growth-promoting molecule termed "L1". MAG in a soluble form, consisting of the extracellular domain of MAG fused to the Fc region of IgG (MAG-Fc) was added to the growing neurons (MAG-Fc; Example 4). As the concentration of MAG-Fc was increased, inhibition of neurite outgrowth increased, while a control chimera, MUC18-Fc, at the same concentration had no effect (FIG. 7a). Furthermore, inhibition of axonal regeneration by MAG-Fc could be reversed by either adding a monoclonal antibody directed against MAG or by desialyating the isolated neurons prior to the assay (FIG. 7b). Soluble MAG-Fc can also inhibit axonal regeneration from cerebellar neurons grown on a monolayer of fibroblasts (FIG. 7c).

Figure 8A:
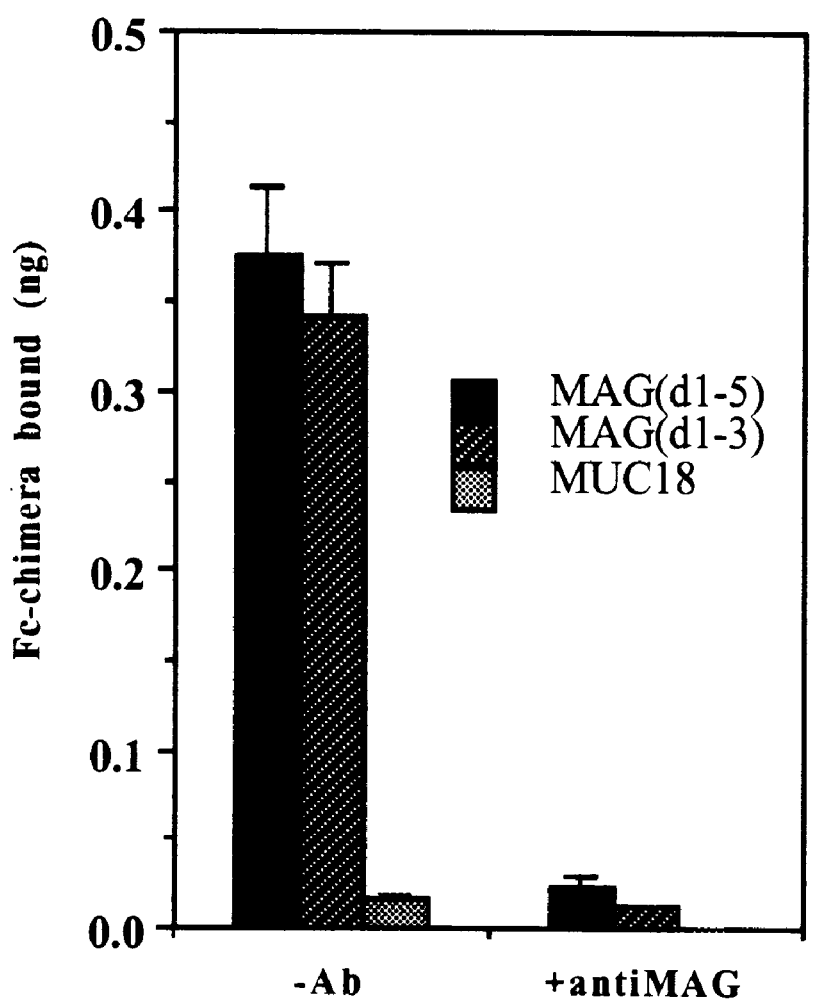
FIG. 8(a). MAG(d1–3)-Fc Binds to Neurons in a Specific, Sialic Acid-dependent Manner. Cerebellar (PND2) neurons vitally labeled with fluorescein were allowed to bind to immobilized MAG(d1–5)-Fc (dark bars), MAG(d1–3)-Fc (hatched bars) or MUC18-Fc (speckled bars), in the presence (+antiMAG) or absence (–Ab) of an anti-MAG monoclonal antibody. Results represent the amount of Fc-chimera bound (ng).

Importantly, using this assay, an inhibitor of MAG activity was identified which can bind to neurons without inhibiting axonal regeneration and can reverse the inhibitory effects of wildtype MAG: A truncated form of MAG-Fc, consisting of the first three, rather than the normal five Ig-like extracellular domains of MAG fused to an IgG Fc domain ("MAG(d1–3)-Fc"; Example 4), specifically bound to cerebellar neurons (FIG. 8a). FIG. 8a shows that soluble Fc chimera consisting of all five ("MAG(d1–5)") or the first three ("MAG(d1–3)") Ig-like domains of MAG could bind to cerebellar neurons from PND2 rats in a reaction which was completely inhibited by the presence of anti-MAG monoclonal antibodies. A control Fc chimeric protein (MUC18) did not bind to neurons either in the presence or absence of anti-MAG antibodies.

Figure 8B:
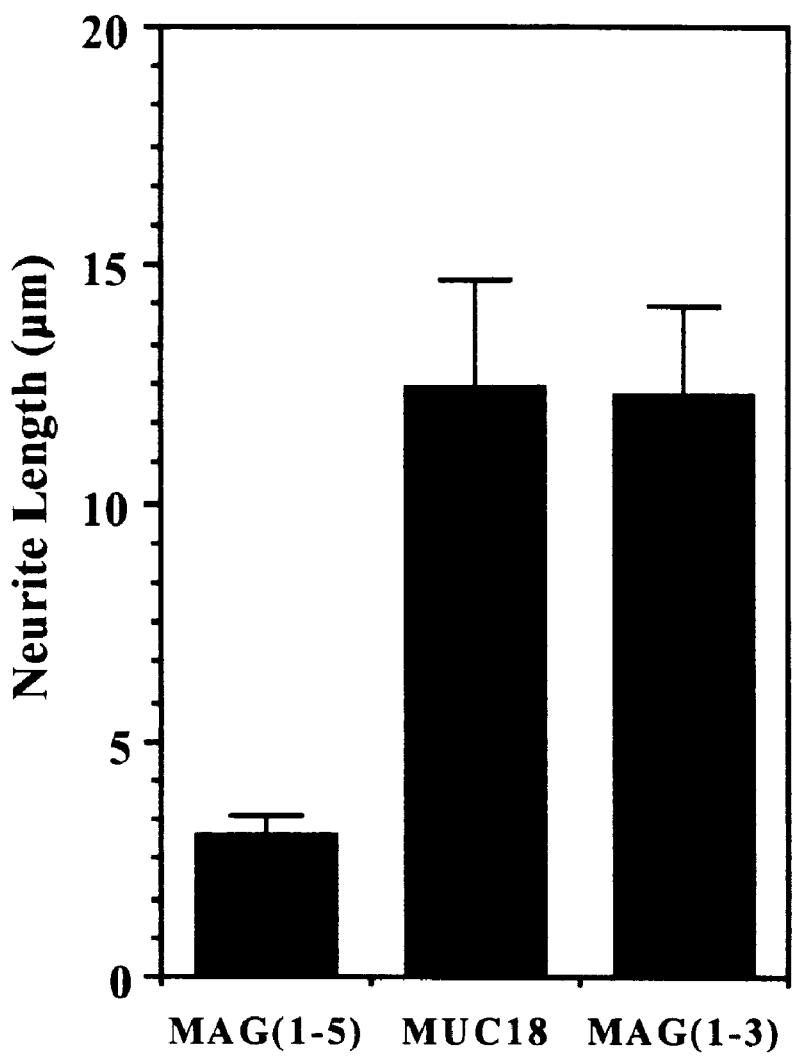
FIG. 8(b). MAG(d1–3)-Fc Does Not Inhibit Axonal Regeneration. Cerebellar neurons were grown on immobilized L1-Fc, in the presence of 50 µg/ml MAG(d1–5)-Fc, Muc18-Fc, or MAG(d1–3)-Fc. Neurite length (µm) was measured as described in FIG. 1. Results represent the average neurite length (µm)±SEM.
Figure 8C:
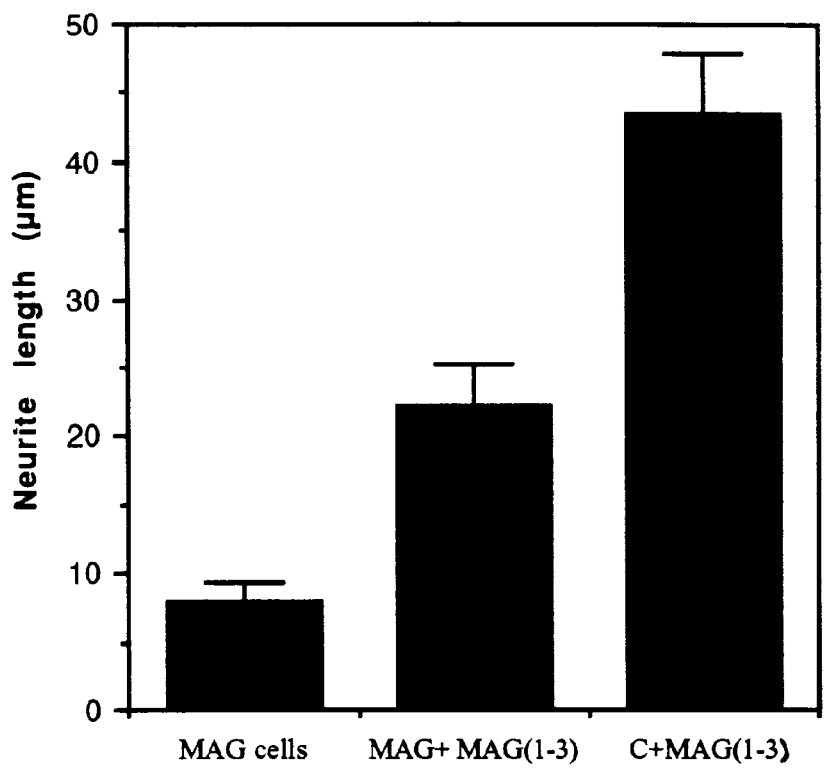
FIG. 8(c). MAG(d1–3)-Fc Reverses Inhibition of Axonal Regeneration by Wildtype MAG Expressed by CHO Cells. Cerebellar neurons (PND2) were grown on MAG-expressing (MAG cells) or control CHO cells, in the presence (+MAG1–3) or absence of MAG(d1–3)-Fc. Neurite length (µm) was measured as described in FIG. 1. Results represent the average neurite length (µm)±SEM.

However, when added to neurons growing on a monolayer substrate of L1, unlike the normal MAG-Fc chimera, MAG(d1–3)-Fc chimera had no effect on axonal regeneration (FIG. 8b). It is thus likely that MAG(d1–3)-Fc can compete with full-length MAG for binding to neurons because MAG(d1–3)-Fc at a concentration of 50 μg/ml can reverse by about 40% inhibition of axonal regeneration by full-length MAG expressed by CHO cells (FIG. 8c).

The above experiments demonstrate that altered and/or mutated forms of soluble MAG which harbor one or more mutations in the MAG molecule that reduce or eliminate its ability to inhibit or promote neurite outgrowth but do not significantly diminish the binding of the altered or mutant form of MAG to neuronal surfaces may be useful inhibitors of MAG activity when administered in vivo (Example 8). The most preferred altered/mutant forms of MAG of the present invention are soluble molecules comprising a truncated form of-MAG-Fc consisting of the first three of the five extracellular Ig-like domains of MAG fused to an immunoglobulin Fc domain ("MAG(d1–3)-Fc").

It is envisioned that other more specific mutations (especially point mutations or small internal deletions) may be made to MAG Ig-like domains that will also reduce or eliminate its ability to inhibit or promote neurite outgrowth without significantly diminishing the binding of the mutant form of MAG to neuronal surfaces. A mutational analysis will likely lead to the identification of a localized "MAG neurite growth signaling site" necessary for activating the downstream cellular signals that are involved in mediating neurite growth regulation. It is envisioned that certain mutations targeted especially to the fourth and fifth domains which are deleted in the MAG(d1–3)-Fc chimeric protein, and/or to the junction between Ig-like domains three and four in MAG will be useful in this regard.

Pharmaceutical Compositions and Treatments Using MAG Derivatives and Inhibitors

The MAG-dependent neurite growth regulating agents of this invention may be formulated into pharmaceutical compositions and administered in vivo at an effective dose to treat the particular clinical condition addressed. Administration of one or more of the pharmaceutical compositions according to this invention will be useful for regulating and for promoting neural growth or regeneration in the nervous system, for treating injuries or damage to nervous tissue or neurons, and for treating neural degeneration associated with traumas to the nervous system, disorders or diseases. Such traumas, diseases or disorders include, but are not limited to: aneurysms, strokes, Alzheimer's disease, Parkinson's disease, Creutzfeldt-Jacob disease, kuru, Huntington's disease, multiple system atrophy, amyotropic lateral sclerosis (Lou Gehrig's disease), and progressive supranuclear palsy.

Determination of a preferred pharmaceutical formulation and a therapeutically efficient dose regiment for a given application is within the skill of the art taking into consideration, for example, the condition and weight of the patient, the extent of desired treatment and the tolerance of the patient for the treatment.

Administration of the MAG derivatives and inhibitors of this invention, including isolated and purified forms, their salts or pharmaceutically acceptable derivatives thereof, may be accomplished using any of the conventionally accepted modes of administration of agents which are used to treat neuronal injuries or disorders.

Soluble altered and mutated forms of MAG such as those described herein are prepared from the culture media of transfected cells, e.g., COS cells (fibroblasts), transfected with expression plasmids encoding the cDNAs for these forms of MAG (Example 4). The soluble MAG molecules, such as MAG-Fc, are secreted by these cells. It is anticipated that, as has been carried out for hybridoma cells that secrete antibodies (Schnell, L. and Schwab, M. E., Nature, 343, pp. 269–72 (1990); Schnell et al., Nature, 367, pp. 170–73 (1993), COS cells or other transfectants secreting the soluble MAG-Fc chimera may be implanted into damaged spinal cord. The cells will secrete MAG-inhibiting forms of altered or mutated MAG-Fc, which prevents the endogenous MAG from interacting with the neuronal surface and thus prevents inhibition of axonal growth and regeneration by endogenous MAG.

About $2 \times 10^6$ transfected cos cells will secrete about 1 mg of MAG-Fc over a 5-day period. A concentration of 50 μg/ml of mutated MAG-Fc effectively reverses the inhibitory effects of wildtype MAG. Finally, within the perineurium of an adult rat spinal cord is a volume of about 0.5 ml. Therefore, if $2 \times 10^6$ mutated or altered MAG-Fc-secreting COS cells are implanted into an injured spinal cord, then the concentration of MAG-Fc should be maintained at about 400 μg/ml, i.e., 8-fold more concentrated than the concentration shown herein to be effective in cultured cells. Finally, calculations to correct for the difference between the volume of the perineurium of an adult rat spinal cord compared to the subject being treated can be made by one of skill in the art. Transfected cells, secreting other "reversing" mutated forms of MAG or MAG "blocking" peptides can be administered to the site of neuronal injury or degeneration in a similar manner.

Likewise, other MAG inhibitors and regulators of this invention, e.g., sialidases and sialyltransferases, free, protein- or lipid-attached sialic acid-bearing sugars, glycopeptides or glycoproteins, can also be delivered by spinal implantation (e.g., into the cerebrospinal fluid) of cells engineered to secrete MAG regulating agents according to this invention. Cell secretion rates of the agent are measured in cell culture and then extrapolated.

Optionally, transfected cells that secrete MAG regulating agents may be encapsulated into immunoisolatory capsules or chambers and implanted into the brain or spinal cord region using available methods that are known to those of skill in the art. See, e.g., WO 89/04655; WO 92/19195; WO 93/00127; EP 127, 989; U.S. Pat. Nos. U.S. Pat No. 4,298, 002; U.S. Pat. No. 4,670,014; U.S. Pat. No. 5,487,739 and references cited therein, all of which are incorporated herein by reference.

For MAG regulating agents that can not be secreted by transfected cells, a pump and catheter-like device may be implanted at the site of injury to administer the agent on a timely basis and at the desired concentration, which can be selected and empirically modified by one of skill in the art. Such pharmaceutical delivery systems are known to those of skill in the art. See, e.g., U.S. Pat. No. 4,578,057 and references cited therein, which are incorporated herein by reference.

The pharmaceutical compositions of this invention may be in a variety of forms, which may be selected according to the preferred modes of administration. These include, for example, solid, semi-solid and liquid dosage forms such as tablets, pills, powders, liquid solutions or suspensions, suppositories, and injectable and infusible solutions. The preferred form depends on the intended mode of administration and therapeutic application. Modes of administration may include oral, parenteral, subcutaneous, intravenous, intralesional or topical administration.

The MAG derivatives and inhibitors of this invention may, for example, be placed into sterile, isotonic formulations with or without cofactors which stimulate uptake or stability. The formulation is preferably liquid, or may be lyophilized powder. For example, the MAG derivatives and inhibitors may be diluted with a formulation buffer comprising 5.0 mg/ml citric acid monohydrate, 2.7 mg/ml trisodium citrate, 41 mg/ml mannitol, 1 mg/ml glycine and 1 mg/ml polysorbate 20. This solution can be lyophilized, stored under refrigeration and reconstituted prior to administration with sterile Water-For-Injection (USP).

The compositions also will preferably include conventional pharmaceutically acceptable carriers well known in the art (see for example Remington's Pharmaceutical Sciences, 16th Edition, 1980, Mac Publishing Company). Such pharmaceutically acceptable carriers may include other medicinal agents, carriers, genetic carriers, adjuvants, excipients, etc., such as human serum albumin or plasma preparations. The compositions are preferably in the form of a unit dose and will usually be administered one or more times a day.

The pharmaceutical compositions of this invention may also be administered using microspheres, liposomes, other microparticulate delivery systems or sustained release formulations placed in, near, or otherwise in communication with affected tissues or the bloodstream. Suitable examples of sustained release carriers include semipermeable polymer matrices in the form of shaped articles such as suppositories or microcapsules. Implantable or microcapsular sustained release matrices include polylactides (U.S. Pat. No. 3,773, 319; EP 58,481), copolymers of L-glutamic acid and gamma ethyl-L-glutamate (Sidman et al., *Biopolymers*, 22, pp. 547–56 (1985)); poly(2-hydroxyethyl-methacrylate) or ethylene vinyl acetate (Langer et al., *J. Biomed. Mater. Res.*, 15, pp. 167–277 (1981); Langer, *Chem. Tech.*, 12, pp. 98–105 (1982)).

Liposomes containing MAG derivatives and inhibitors can be prepared by well-known methods (See, e.g. DE 3,218,121; Epstein et al., *Proc. Natl. Acad. Sci. U.S.A.*, 82, pp. 3688–92 (1985); Hwang et al., *Proc. Natl. Acad. Sci. U.S.A.*, 77, pp. 4030–34 (1980); U.S. Pat. Nos. 4,485,045 and 4,544,545). Ordinarily the liposomes are of the small (about 200–800 Angstroms) unilamellar type in which the lipid content is greater than about 30 mol. % cholesterol. The proportion of cholesterol is selected to control the optimal rate of MAG derivative and inhibitor release.

The MAG derivatives and inhibitors of this invention may also be attached to liposomes, which may optionally contain other agents to aid in targeting or administration of the compositions to the desired treatment site. Attachment of MAG derivatives and inhibitors to liposomes may be accomplished by any known cross-linking agent such as heterobifunctional cross-linking agents that have been widely used to couple toxins or chemotherapeutic agents to antibodies for targeted delivery. Conjugation to liposomes can also be accomplished using the carbohydrate-directed cross-linking reagent 4-(4-maleimidophenyl) butyric acid hydrazide (MPBH) (Duzgunes et al., *J. Cell. Biochem.* Abst. Suppl. 16E 77 (1992)).

Utility of MAG Derivatives and Inhibitors

The discovery that MAG is a potent inhibitor of axonal regeneration has potential clinical use in the situations of nervous system injury—both of the peripheral and central nervous systems—and in particular for CNS injury. The mammalian central nervous system does not regenerate after injury even though there are many molecules present that promote and encourage a nerve to grow. The result is paralysis or brain damage. It has been shown that there are molecules present in the adult CNS that will actively prevent a nerve from regenerating. It is anticipated that if these inhibitory molecules can be first identified and subsequently blocked, then an environment permissive for regeneration could be engineered.

The first step is to identify what the inhibitory molecules are. MAG is the first such molecule to be identified in myelin. Using the assay systems established herein to monitor the inhibitory effects of MAG, strategies can now be designed with MAG as a target such that its inhibitory function is blocked. Such an agent can then be administered to damaged nerves reversing the inhibitory effects of MAG in vivo and allowing nerve regeneration to proceed.

The assays of the present invention are useful for identifying agents likely to reverse inhibition of nerve regeneration by MAG. Using the assay systems described herein, the inhibitory effects of MAG were shown to be blocked/prevented from functioning by agents such as sialidases or small sialic acid-bearing sugars and by soluble, mutated forms of MAG. These agents, or modified forms of these agents that can either increase or decrease their affinity for MAG or for its receptor, may be administered to damaged nerves, reversing the inhibitory effects of MAG in vivo and allowing regeneration to proceed.

In addition, the properties of MAG as a negative guidance cue can be used to guide regenerating axons to their correct target and keep them on the correct path. For this purpose, MAG, or different domains of MAG, can be administered to the precise regions of the regenerating nervous tissue to contain growth along exact pathways.

As shown herein, MAG binds to a sialic acid-bearing glycoprotein on neurons to bring about inhibition of nerve growth and regeneration in a wide variety of neuronal cell types. And also as shown herein, when the sialic acid residues of neurons are removed with enzymes termed sialidases, these inhibitory effects of MAG are reversed. Similarly, small sialic acid-bearing sugars and derivatives thereof can bind to MAG, prevent it from interacting with the sialic acid glycoprotein on neurons and prevent its inhibition of axonal regeneration. It is anticipated that in vivo, after injury, application of MAG inhibitors such as sialidases, free-small sialic-bearing sugars or modifications of sialic acid attached to other sugars, small sialic acid-bearing sugars covalently attached to protein carrier molecules or lipids or small sialic acid glycoproteins or glycopeptides, either individually or in various combinations, will block the inhibitory effects of MAG and/or other inhibitory molecules that act through a sialic acid-bearing receptor, and encourage axonal regeneration to take place. Similarly, small peptides or peptide fragments of MAG , mutated and altered forms of MAG and antibodies to MAG may block the interaction of endogenous MAG with neurons and allow nerve regeneration.

As shown herein, a mutated, soluble form of MAG can bind to neurons, but itself does not inhibit axonal growth. Importantly, this mutated form of MAG can reverse the inhibitory effects of wildtype MAG.

Finally, it is envisioned that MAG, MAG derivatives and MAG inhibitors may be used as a guidance cue in precise regions of the regenerating nervous system to keep growing axons on the correct path and moving towards the correct target.

All references cited herein are hereby incorporated by reference.

The following are examples which illustrate the methods of this invention used to identify the MAG-dependent neurite growth altering agents, compositions of this invention which comprise such agents, and methods comprising the administration of those compositions. These examples should not be construed as limiting: the examples are included for the purposes of illustration only and the present invention is limited only by the claims.

EXAMPLE 1

Isolation of Different Neuronal Cell Types

Neurons were isolated essentially as described in Doherty et al., Nature, 343, pp. 464–66 (1990); Neuron, 5, pp. 209–19 (1990); and Kleitman et al., Culturing Nerve Cells, pp. 337–78, MIT Press, Cambridge, Mass./London, England (G. Banker and K. Goslin, Eds.) (1991). Briefly, for animals up to nine days of age, the cerebellum, retina, hippocampus, and spinal cord were removed from two animals. Like tissue was combined and placed in 5 ml of 0.025% trypsin in PBS, triturated, and incubated for a further 10 minutes (min.) at 37° C. Trypsinization was stopped by addition of 5 ml DMEM containing 10% fetal calf serum (FCS) and cells were centrifuged at 800 rpm for 6 min. The cells were resuspended to a single cell suspension in 2 ml of SATO containing 2% FCS. For DRG and SCG neurons, ganglia were removed from two animals and incubated in 5 ml of L15 medium containing 0.025% trypsin and 0.3% collagenase type I (Worthington) for 30 min. at 37° C. The ganglia were triturated with a fire-polished Pasteur pipette. Trypsinization was stopped by adding 5 ml of DMEM containing 10% FCS, centrifuged at 800 rpm for 6 min., and resuspended in 2 ml of SATO containing 2% FCS. Cells were counted with a Coulter counter.

EXAMPLE 2

Neurite Outgrowth Assays on Transfected CHO cells

Expression of MAG by Transfected CHO Cells

Chinese hamster ovary (CHO) cells deficient in the dihydrofolate reductase (dhfr) gene (Urlaub and Chasin, Proc. Natl. Acad, Sci. USA, 77, pp. 4216–20 (1980)) were transfected with a MAG-cDNA expression plasmid with the dhfr gene and the L-MAG cDNA in either a 5'-3' or, as a control, a 3'-5' orientation, cells with multiple copies of dhfr were selected by growing in increasing concentrations of methotrexate, and the expression of MAG by individual transfected CHO cell lines characterized as described in Mukhopadhyay et al., Neuron, 13, pp. 757–67 (1994), which is incorporated herein by reference. Transfected cells were maintained in DMEM supplemented with 10% dialyzed FCS, proline (40 mg/liter), thymidine (0.73 mg/liter), and glycine (7.5 mg/liter) at 37° C. in 5% $CO_2$.

The MAG-expressing transfected CHO cell line ("CHO-MAG2") described as MAG2 in that publication was deposited on Jun. 27, 1996 with the American Type Culture Collection (ATCC) (Rockville, Md.) according to the provisions of the Budapest Treaty, and was assigned the ATCC accession number designated: [CRL-12145]. All restrictions on the availability to the public of the above ATCC deposit will be irrevocably removed upon the granting of a patent on this application.

Neurite Outgrowth Assays

Confluent monolayers of control and MAG-expressing CHO cells were established over a 24-hour (h) period in individual chambers of an 8-well tissue culture slide (Lab-Tek). Co-cultures were established as described previously (Doherty et al., Nature, 343, pp. 464–66 (1990); Neuron, 5, pp. 209–19 (1990); Mukhopadhyay et al., Neuron, 13, pp. 757–67 (1994)) by adding approximately 5000 cerebellar, dorsal root ganglion (DRG) and superior-cervical ganglion (SCG) neurons and 10,000 retinal, hippocampal and spinal cord cells to the CHO monolayers. Culture medium was SATO containing 2% FCS. Where indicated, 20 mU of VCS was included throughout the coculture period (see Example 4), or monolayers were incubated with small oligosaccharides for one hour before adding the neuronal cell suspension and included throughout the coculture period. After periods of time as indicated, the cocultures were fixed for 30 min with 4% paraformaldehyde and permeabilized with ice-cold methanol for 2 min. The cells were then blocked for 30 min with DMEM containing 10% FCS and incubated for 2 h with a rabbit polyclonal antibody against the neuronal marker GAP43 (1:4000). Cells were washed three times with PBS-BSA (2%) and then incubated for 30 min at room temperature with a biotinylated donkey anti-rabbit Ig (1:300, Amersham), washed three times, and incubated with streptavidin-conjugated Texas Red (1:300, Amersham) for 30 min. After three more washes, the slides were mounted in Permfluor (Baxter) and viewed with a Zeiss fluorescent microscope. The length of the longest neurite for each GAP43-positive neuron was determined using the Biological Detection System image analysis program (Pittsburgh).

Alternatively, other neuron-specific antibodies such as anti-neurofilament monoclonal antibodies, which are commercially available (e.g., Boehringer Mannheim, Sigma Immunochemicals), may be used starting at dilutions recommended by the manufacturer. The appropriate species-specific, biotinylated anti-Ig secondary antibody is then selected according to the species in which the primary anti-neural antibody was generated. In addition, various vital dyes (e.g., Molecular Probes, Oregon) which stain neurites may be used in this assay in place of a fluorescent neural-specific antibody.

EXAMPLE 3

Neurite Growth Assays with CHO Cells to Test Putative MAG-dependent Neurite Growth Altering Agents The transfected CHO cell assay described in Example 2 may also be used to screen and identify agents that alter neurite growth properties of a particular neuronal cell type and age in a MAG-dependent fashion. Neurite outgrowth was compared for cerebellar (TABLE 1) and DRG (TABLE 2) neurons from PND 2 animals, grown on MAG-expressing and control CHO cells as described in Example 2. Where indicated, small sialic acid-bearing sugars were included in the co-cultures at increasing concentrations. 100% inhibition was taken as the difference in length of neurites on control and MAG-expressing CHO cells. Results are the mean of at least two experiments, with at least 150 neurons measured for each experiment. DD-NANA=2,3-dideoxy sialic acid; SL=sialo 2,3-α lactose.

This assay may be used to test other putative MAG-dependent neurite growth regulating agents by including them in the coculture and measuring their effect in the presence and absence of cell-surface MAG as described above for the small sialic acid-bearing sugars.

EXAMPLE 4

Binding of Soluble MAG-Fc Chimeras to Neurons
Production of Immunoglobulin Fc-chimeric proteins Expression plasmids encoding various forms of MAG-Fc (such as those referred to herein as MAG[d1–5]-Fc), MAG [d1–3]-Fc and a control Fc-chimeric protein MUC 18-Fc) were prepared as described in Kelm et al., *Current Biol.*, 4, pp. 965–72 (1994) and references cited therein. For discussions and a general protocol for making soluble recombinant adhesin molecules, see D. L. Simmons, "Cloning cell surface molecules by transient expression in mammalian cells," in *Cellular Interactions in Development—A Practical Approach*, pp. 118–125, IRL Press, Oxford (Ed. D. A. Hartley) (1993); *Development (Supp.)*, pp. 193–203 (1993); and P. R. Crocker and S. Kelm, "Methods for studying the cellular binding properties of lectin-like receptors," in *Handbook of Experimental Immunology*, pp. 1–30 (1995), which are incorporated herein by reference.

*E. coli* cell samples transformed with plasmids that express the MAG[d1–5]-Fc, MAG[d1–3]-Fc and MUC18-Fc chimeric proteins described in Kelm et al., supra, were deposited on Jun. 27, 1996 with the American Type Culture Collection (ATCC) (Rockville, Md.) according to the provisions of the Budapest Treaty, and were assigned the ATCC accession numbers designated as shown below:

| CELL LINE | ATCC Accession No. |
|---|---|
| a) MAG[1–3]-Fc | 98089 |
| b) MAG[1–5]-Fc | 98090 |
| c) MUC18-Fc | 98088 |

All restrictions on the availability to the public of the above ATCC deposits will be irrevocably removed upon the granting of a patent on this application.

Binding of Fc-Chimeras to Neurons

Plasmids encoding MAG-Fc, MAG[d1–3]-Fc and MUC 18-Fc were transfected into COS cells and the Fc-chimeric proteins purified from the media as described in Kelm et al., *Current Biol.*, 4, pp. 965–72 (1994) and P. R. Crocker and S. Kelm, "Methods for studying the cellular binding properties of lectin-like receptors," in *Handbook of Experimental Immunology*, pp. 1–30 (1995).

Neuron binding assays were performed essentially as described in DeBellard et al., *Mol. Cell. Neuroscience*, 7, pp. 89–101 (1996), which is incorporated herein by reference. Fc-chimeric proteins were adsorbed for 3 h at 37° C. to wells of microtiter plates that had been coated for 2 h at 37° C. with anti-human IgG at 15 µg/ml in 0.1M bicarbonate buffer, pH 9.6. Prior to the binding assay, neurons were vitally labeled with the fluorescent dye calcein AM (Molecular Probes) by incubating $2 \times 10^6$ neurons in 5 ml of 10 µM calcein AM in PBS for 15 min at 37° C. before being washed and resuspended in PBS. Where indicated, a monoclonal antibody directed against MAG (Boehringer Mannheim) was included in the assay at a concentration of 10 µg/ml, and where indicated, neurons were desialyated before being used. One hundred µl of a suspension of vitally labeled neurons, containing $1–2 \times 10^5$ cells was added to each well and allowed to incubate for 1 h at room temperature. The plates were washed three times with PBS applied to each well under gravity and the fluorescence was measured in a FluorImager (Molecular Dynamics).

EXAMPLE 5

Neurite outgrowth Assays on a Growth Permissive Substrate in the Presence or Absence of MAG-Fc Chimera Growth Permissive Substrate comprising an L1-Fc Chimera The L1 glycoprotein is a cell adhesion molecule (CAM) expressed on the surface of a wide variety of mammalian neuronal cell types which stimulates neurite outgrowth. Soluble L1-Fc chimera may be constructed using procedures known to those of skill in the art (such as those cited in Example 3; Doherty et al., *Neuron*, pp. 57–66 (1995), incorporated herein by reference). Soluble L1-Fc chimera, when presented to neurons, are as effective at promoting neurite outgrowth as the normal cell surface-associated L1 (Doherty et al., supra, and references cited therein which are incorporated herein by reference). As described in Doherty et al., L1-Fc chimera can stably associate with the surface of fibroblast 3T3 cells or polylysine/collagen or polylysine/ fibronectin-coated substrates.

Individual wells of an eight-chamber tissue culture plastic slide (Lab-Tek, Nuc. Inc.) were incubated with 0.3 ml of 16.6 µg/ml poly-1-lysine in sterile water for at least one hour under sterile conditions. Each well was washed twice with 400 µl of a 0.1M sodium bicarbonate solution, pH 9.6, and then received 0.3 ml of 0.1M sodium bicarbonate solution, pH 9.6, containing 15 µg/ml goat anti-human IgG (Fc-specific) monoclonal antibody (Sigma). The wells were incubated for 2 h at 37° C., and washed three times with 0.4 ml of ice-cold DMEM. Each well then received 0.3 ml of DMEM containing 40 µg/ml of L1-Fc and was incubated for 2–4 hours at 37° C. The wells were washed twice DMEM.

Neurite Outgrowth on L1-Fc Substrate
A Soluble MAG-Fc Binding Assay

Cerebellar neurons (post-natal days 2–7) were dissociated by trypsinization as described in Example 1, except that the dissociated neurons were resuspended in 5 ml of SATO medium containing 2% dialyzed FBS. To an individual well coated with a monolayer of L1-Fc as described above, $5.0 \times 10^4$ cerebellar neurons were added, followed by either a single concentration (about 50 µg/ml) or increasing concentrations (e.g., 0–30 µg/ml) of MAG-Fc or MUC18-Fc chimeric soluble proteins, depending on the experiment. Neurons were cultured overnight (about 16 h) at 37°0 C., and then fixed and stained essentially as described in Example 2.

EXAMPLE 6

Neurite Outgrowth Assays Using Soluble MAG To Identify MAG-Dependent Neurite Growth Altering Agents The neurite outgrowth binding assay using soluble MAG-Fc described in Example 5 may also be used to perform competitive neuron binding/growth experiments to screen and identify new agents that alter the neurite growth properties of a particular neuronal cell type and age in a MAG-dependent fashion. One or more concentrations of the test agent were included in the cocultures of Example 5, and the effect of the test agent in the presence and absence of soluble MAG assessed.

EXAMPLE 7

Neurite Outgrowth Assays With Desialyated Neurons

Single cell suspensions of different neurons at various postnatal ages were washed and resuspended in phosphate-buffered saline (PBS). Approximately $2 \times 10^6$ cells were incubated with 50 mU of *Vibrio cholera* sialidase (VCS, Calbiochem) (a neuraminidase) in a final volume of 0.5 ml for 2 hours at 37° C. Neurons were washed with PBS and resuspended in SATO medium containing 2% FCS for neurite outgrowth experiments, or in PBS for neurite binding assays.

This procedure may be modified by using enzymes other than sialidase that digest or otherwise modify carbohydrate structures (see, e.g., Kelm et al., *Carbohydr. Res.,* 149, pp. 59–64 (1986), which is incorporated by reference herein). For example, sialyl transferases may be employed to alter or remove sialyated glycans on neuronal surfaces comprising sialic acid residues having a Neu5Acα2→3Galβ1→3GalNAc (3-O) structure to which MAG binds.

EXAMPLE 8

In Vivo Delivery of MAG-Dependent Neurite Growth Altering Agents

COS cells transfected with an expression plasmid that encodes MAG(d1–3)-Fc were cultured and the cultures assayed for the rate of MAG(d1–3)-Fc secretion. Approximately $2\times10^6$ cells—which secrete about 1 mg of MAG (d1–3)-Fc over a 5-day period—are surgically implanted into the cerebrospinal fluid surrounding the spinal cord of an injured subject in the vicinity of nerve damage in need of repair. Optionally, repeated administrations are performed. The cells secrete MAG(d1–3)-Fc, which is capable of inhibiting endogenous MAG activity in the myelin of the implant site, and neural regeneration is stimulated.

What is claimed is:

1. A composition which comprises a pharmaceutically acceptable carrier and at least one MAG inhibitor in an amount effective for altering neural growth or regeneration in the nervous system, wherein the MAG inhibitor is a soluble chimeric protein which comprises extracellular Ig-like domains one to three of MAG.

2. The composition according to claim 1, wherein the MAG inhibitor is MAG(d1–3)-Fc.

3. A composition which comprises a pharmaceutically acceptable carrier and at least one MAG inhibitor in an amount effective for altering neural growth or regeneration in the nervous system, wherein the MAG inhibitor is a soluble chimeric protein which comprises extracellular Ig-like domains one to five of MAG.

4. The composition according to claim 3, wherein the MAG inhibitor is MAG(d1–5)-Fc.

5. The composition according to any one of claims 1–4, wherein the MAG inhibitor can inhibit the binding of endogenous MAG to neurons in the CNS or PNS.

6. A method for regulating neural growth or regeneration in the nervous system which comprises the step of administering, in a manner which can affect the nervous system, a composition according to any one of claims 1–4.

7. The method according to claim 6, wherein neural growth or regeneration is promoted.

8. A method for treating injuries or damage to nervous tissue or neurons which comprises the step of administering, in a manner which can affect the nervous system, a composition according to any one of claims 1–4.

9. A method for treating neural degeneration associated with a disorder or disease which comprises the step of administering, in a manner which can affect the nervous system, a composition according to any one of claims 1–4.

10. A soluble chimeric protein which comprises extracellular Ig-like domains one to three of MAG.

11. The MAG inhibitor MAG(d1–3)-Fc.

12. A soluble chimeric protein which comprises extracellular Ig-like domains one to five of MAG.

13. The MAG inhibitor MAG(d1-5)-Fc.

* * * * *